(12) United States Patent
Mohamed

(10) Patent No.: US 7,777,504 B2
(45) Date of Patent: Aug. 17, 2010

(54) SENSOR FOR DETERMINING THE ELECTRIC PROPERTIES OF A SAMPLE

(76) Inventor: Moustafa Mohamed, Physics Department, UNBC, 3333 University Way, Prince George, British Columbia (CA) V2N 4Z9

( * ) Notice: Subject to any disclaimer, the term of this patent is extended or adjusted under 35 U.S.C. 154(b) by 18 days.

(21) Appl. No.: 11/254,454

(22) Filed: Oct. 20, 2005

(65) Prior Publication Data

US 2006/0114006 A1   Jun. 1, 2006

(30) Foreign Application Priority Data

Nov. 26, 2004   (CA) ............................ 2,486,562

(51) Int. Cl.
  *G01R 27/26* (2006.01)
(52) U.S. Cl. .................. 324/690; 324/676; 324/686; 324/691; 324/696
(58) Field of Classification Search ................ 324/642, 324/664, 690, 658, 694, 696, 710, 711, 689, 324/360, 677, 686, 640
See application file for complete search history.

(56) References Cited

U.S. PATENT DOCUMENTS

| | | | |
|---|---|---|---|
| 3,175,151 A * | 3/1965 | Gurry .......................... | 324/678 |
| 3,757,210 A | 9/1973 | Hansen et al | |
| 3,771,548 A * | 11/1973 | Rauchwerger .............. | 137/392 |
| 3,936,735 A * | 2/1976 | deBough .................... | 324/664 |
| 3,968,428 A * | 7/1976 | Numoto ...................... | 324/694 |
| 4,540,936 A | 9/1985 | Walsh | |
| 4,693,419 A | 9/1987 | Weintraub et al. | |
| 4,837,499 A | 6/1989 | Scherer, III | |
| 4,909,070 A | 3/1990 | Smith | |
| 4,918,375 A * | 4/1990 | Malicki et al. .............. | 324/642 |
| 4,941,501 A | 7/1990 | Bireley | |
| 4,952,868 A | 8/1990 | Scherer, III | |
| 5,424,649 A * | 6/1995 | Gluck et al. ................. | 324/667 |
| 5,479,104 A | 12/1995 | Cambell | |
| 5,514,973 A * | 5/1996 | Byler et al. .................. | 324/695 |
| 5,621,669 A * | 4/1997 | Bjornsson .................... | 702/85 |
| 5,792,938 A | 8/1998 | Gokhfeld | |
| 5,859,536 A * | 1/1999 | Stockton ...................... | 324/664 |
| 6,073,480 A | 6/2000 | Gokhfeld | |
| 6,401,742 B1 | 6/2002 | Cramer et al. | |
| 6,441,622 B1 * | 8/2002 | Wrzesinski et al. ......... | 324/643 |
| 6,657,443 B2 | 12/2003 | Anderson | |
| 6,703,847 B2 | 3/2004 | Venter et al. | |
| 7,126,352 B2 * | 10/2006 | Bernhard ..................... | 324/664 |

OTHER PUBLICATIONS

Draft 11-254454 Amendments, Jay Franklin, emailed on Feb. 3, 2009, p. 1-11.*

* cited by examiner

*Primary Examiner*—Thomas Valone
(74) *Attorney, Agent, or Firm*—Davis & Bujold, P.L.L.C.

(57) ABSTRACT

An apparatus for determining the electric properties of a sample. The apparatus includes a probe having an input, an output, and an effective resistance, inductance and/or capacitance dependent upon the properties of the sample; a pulse generator for producing pulses connected to the input of the probe, each pulse having a period of a sufficient duration to allow the probe to reach steady state; and a measuring device connected to the output of the probe and configured to output a representation of the sample properties based on the effective resistance, inductance and/or capacitance of the probe.

17 Claims, 3 Drawing Sheets

SENSOR FOR DETERMINING THE ELECTRIC PROPERTIES OF A SAMPLE

FIELD OF THE INVENTION

The present invention relates to an apparatus for determining properties of a sample, in particular, the moisture content, salinity, resistance, inductance and capacitance.

BACKGROUND OF THE INVENTION

Moisture sensors are commonly used to determine the moisture content of soils or other materials. These devices are useful, for example, for scientific applications, or for determining a watering schedule. Different techniques are used by these sensors. One common technique used, for example by U.S. Pat. No. 4,941,501, is to connect a probe in a circuit, insert the probe into the material, and find the resonant frequency of the circuit. As the probe acts as a capacitor, the capacitance will change depending on the dielectric properties of the material within the probe, with the resonant frequency allowing the user to determine the capacitance. Probes used in moisture sensors can be in various shapes, such as with two separate conductors in coaxial form, as in U.S. Pat. No. 5,479,104, or with separate conductors in a parallel configuration, such as in U.S. Pat. No. 4,909,070.

SUMMARY OF THE INVENTION

According to an aspect of the invention, there is provided an apparatus for determining the properties of a sample such as the moisture content, salinity, electric resistance, inductance and capacitance, and a method for using the same. The apparatus comprises a probe having an input, an output, and an effective capacitance dependent upon the properties of the sample; a pulse generator, which produces pulses such as pulses with a square leading edge, is connected to the input of the probe, each pulse having a period of a sufficient duration to allow the probe to reach steady state; and a measuring device connected to the output of the probe and configured to output a representation of the properties of the sample based on the effective capacitance of the probe. The probe may also have an effective resistance, and the measuring device may then be configured to output the properties of the sample based on the effective capacitance and the effective resistance of the probe.

The measuring device may comprise a resistive element and a capacitive element connected in parallel to the resistive element, such that the effective resistance is dependent upon the steady state voltage of the capacitive element and/or a diode connected in series with a capacitive element, the diode and the capacitive element being connected in parallel to the resistive element, such that the effective capacitance of the probe is proportional to the voltage drop on the capacitive element connected in series with the diode. The measuring device may also comprise a microprocessor. The device may include plural probes, the input of each probe being connected to a pulse generator and the output of each probe connected to a measuring device, and at least one probe are coated by an electrically insulative material and the conductors of at least one probe are not coated by electrically insulative material.

BRIEF DESCRIPTION OF THE DRAWINGS

These and other features of the invention will become more apparent from the following description in which reference is made to the appended drawings, the drawings are for the purpose of illustration only and are not intended to in any way limit the scope of the invention to the particular embodiment or embodiments shown, wherein.

DETAILED DESCRIPTION OF THE PREFERRED EMBODIMENT

Figure 1:
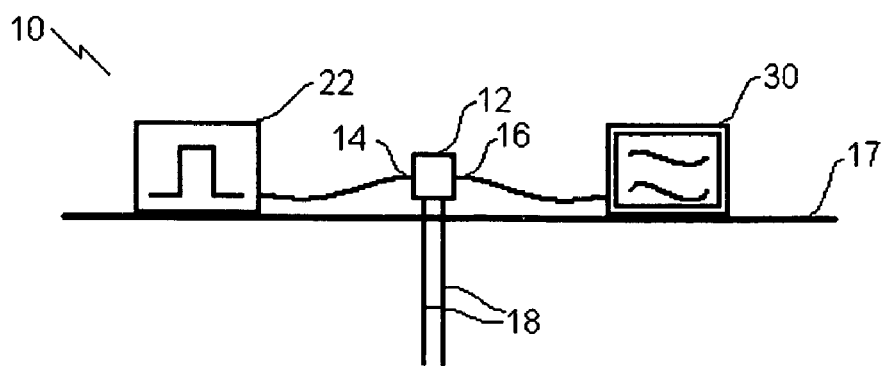
FIG. 1 is a block diagram of the apparatus for determining properties of a sample constructed in accordance with the teachings of the present invention.

The preferred embodiment, an apparatus for determining properties of a sample generally identified by reference numeral 10, will now be described with reference to FIGS. 1 through 10.

Figure 2:
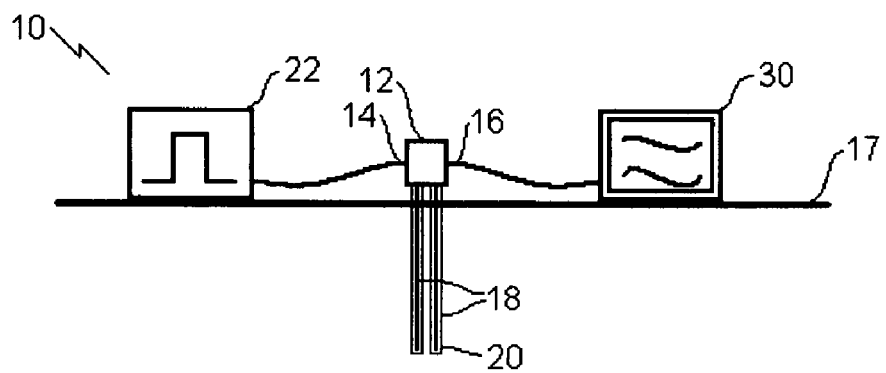
FIG. 2 is a block diagram of the apparatus constructed in accordance with the teachings of the present invention.
Figure 3:
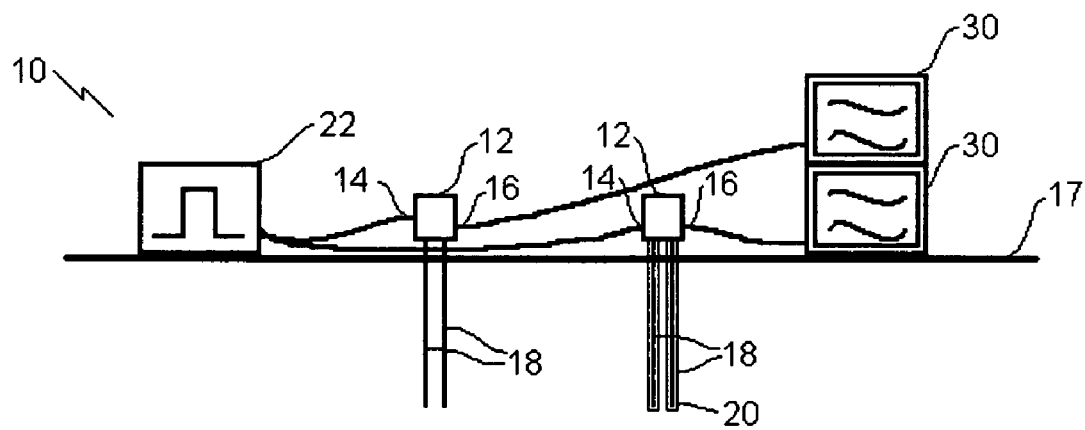
FIG. 3 is a block diagram of the apparatus using more than one probe.

Structure and Relationship of Parts:

Referring now to FIG. 1, there is shown apparatus for determining properties of a sample 10. Apparatus 10 is capable of determining the properties of a sample such as moisture content, salinity, resistance, inductance, and capacitance. The inducatance may be found as it is related to the capacitance. Apparatus 10 comprises a probe 12 having an input 14, an output 16. Probe 12 is formed of two conductors 18 spaced apart at a known distance d, and is adapted to be inserted into a sample 17 that has properties to be measured. While two parallel conductors 18 are shown, it will be understood that other configurations of conductors 18 are possible as are known in the art, such as a coaxial arrangement. As conductors 18 are spaced apart, probe 12 will have an effective capacitance and an effective resistance dependent upon the properties of the sample 17, and based on the distance between conductors 18. Referring to FIG. 2, conductors 18 may also be coated in an electrically insulative material 20, such as varnish, plastics or the like, so that the effective resistance of the probe can be approximated as infinity.

Figure 4:
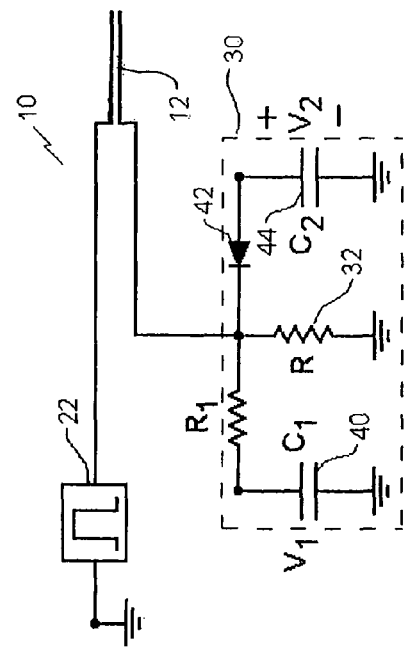
FIG. 4 is a representative circuit diagram of the apparatus.
Figure 8:
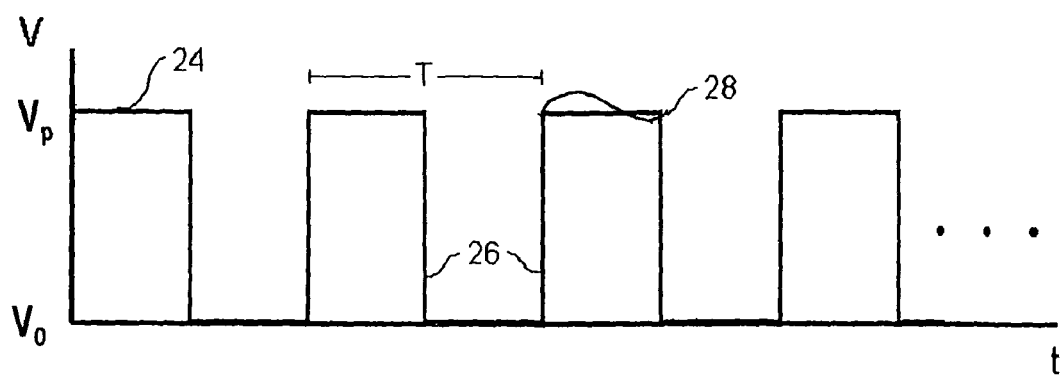
FIG. 8 is a waveform of the input controller signal.
Figure 9:
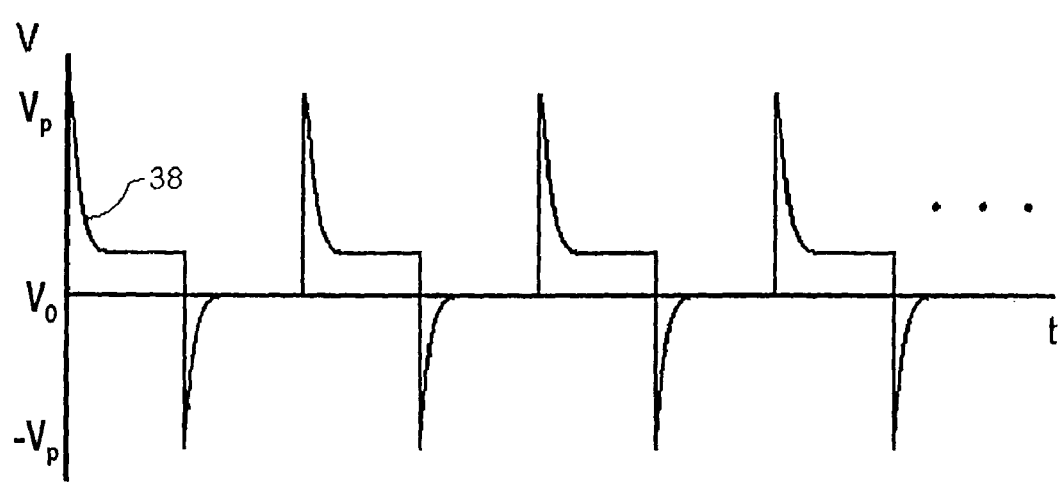
FIG. 9 is a waveform across the resistive element of the measuring device.
Figure 10:
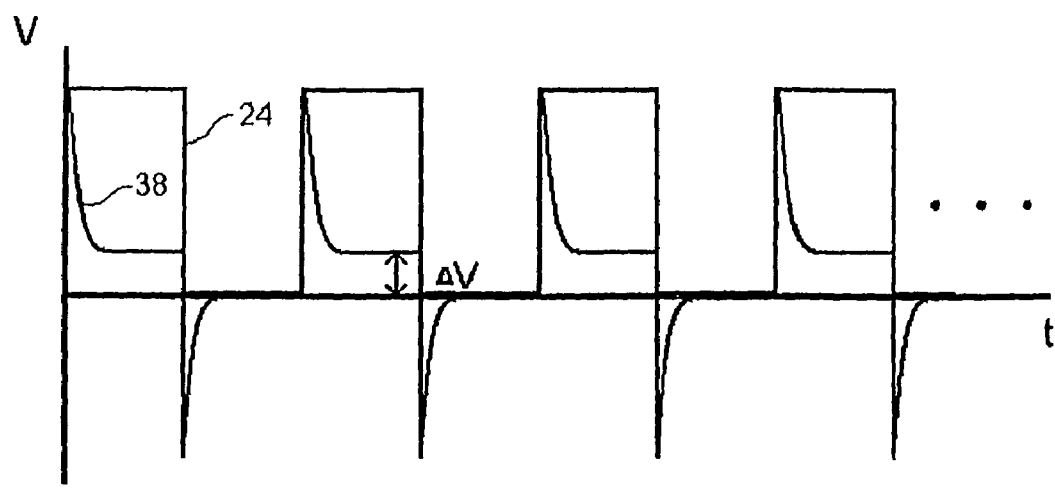
FIG. 10 is the waveforms shown in FIGS. 7 and 8 superimposed.

A pulse generator 22 that produces electrical pulses 24 is connected to input 14 of probe 12. Referring to FIG. 8, the waveform 26 at input 14 is shown. It can be seen that pulses 24 have a square leading edge 28, which is preferable. Pulses 24 are also required to have a period T of a sufficient duration to allow probe 12 to reach steady state, both in the charging and discharging cycles. Referring again to FIGS. 1 and 2, a measuring device 30 is connected to output 16 of probe 12 and is configured to output the properties of sample 17 based on the effective capacitance and/or the effective resistance of probe 12. Referring now to FIG. 4, measuring device is represented as resistor 32 having resistance R, and the sample's effective capacitance and effective resistance are represented by capacitor 34 having capacitance $C_{eff}$ and resistor 36 having resistance $R_{eff}$, respectively. Referring now to FIG. 9, the waveform 38 across resistor 36 is shown. Referring now to FIG. 10, waveforms 26 and 38 are shown. From this, we can determine the effective resistance $R_{eff}$ and the effective capacitance $C_{eff}$, as explained below.

When capacitor 34 is fully charged, then it acts as an open circuit, and the current I is the same in both R and $R_{eff}$.

$$I = V_R/R = V_{sample}/R_{eff}$$

where $V_R = \Delta V$ in FIG. 10, and $$V_{sample} = V_{applied} - V_R = V_{applied} - \Delta V$$

Therefore:

$$\Delta V/R = (V_{applied} - \Delta V)/R_{eff}$$

By rearranging, we can get $R_{eff}$ as:

$$R_{eff} = [(V_{applied}/\Delta V) - 1]R$$

So, by measuring $\Delta V$, knowing R and $V_{applied}$, one can calculate the effective resistance $R_{eff}$.

Figure 5:
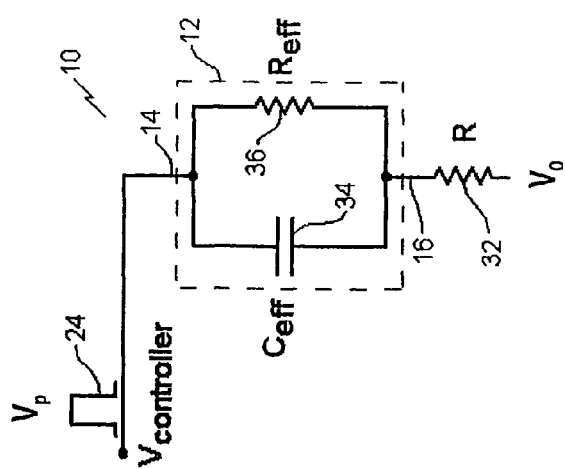
FIG. 5 is a representative circuit diagram of the apparatus during the discharge cycle.

The effective capacitance $C_{eff}$ may be found by analyzing the discharging curve. During the discharging cycle, the equivalent circuit is shown in FIG. 5. In this case, R and $R_{eff}$ are in parallel. Therefore:

$$R_{discharge} = [R \cdot R_{eff}/(R + R_{eff})]$$

We also know that the relationship between the voltage drop across a discharging capacitor and time t is:

$$V_C(t) = V_{max} e^{(-t/R_{discharge} \cdot C)}$$

Therefore:

$$\ln[V_C(t)/V_{max}] = -[t/R_{discharge} \cdot C_{eff}]$$

So, the effective capacitance may be calculated by measuring $V_C(t)$, knowing that:

$$V_{max} = V_{applied} - \Delta V.$$

Figure 6:
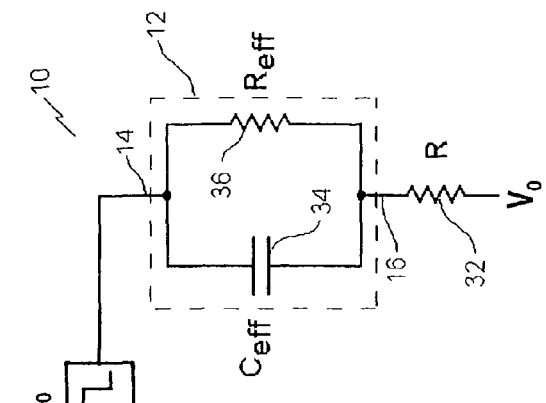
FIG. 6 is a schematic diagram of a preferred embodiment of the apparatus.
Figure 7:
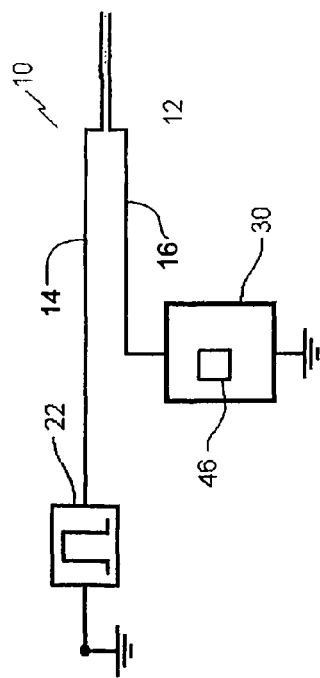
FIG. 7 is a schematic diagram of an alternative embodiment of the apparatus.

Referring now to FIG. 6, a description of a preferred embodiment of measuring device 30 will be described. $\Delta V$, or the steady state voltage, may be measured by connecting a resistive element such as resistor 32 in parallel with resistance $R_1$ and a capacitive element such as capacitor 40 having capacitance $C_1$. Capacitor 40 acts as a simple integrator, such that the positive side of the charging cycle will cancel the negative side of the discharging cycle, leaving $\Delta V$. During the discharging cycle, $V_C$ can be measured by connecting a diode 42 in series with a capacitive element such as capacitor 44 with capacitance $C_2$, where diode 42 and capacitor 44 are in parallel with resistor 32. Diode 42 acts as a gate, allowing only the discharging cycle to charge capacitor 44, which acts as a simple integrator. The voltage drop $V_2$ can then be calibrated to measure C for a given sample, $C_{eff}$. Referring to FIG. 7, an alternative embodiment of measuring device 30 is a microprocessor 46. Microprocessor 46 could then be programmed to follow a similar analysis to that described above.

It was found by experiment that the voltage drop $V_2$ on capacitor 44 depends on both the capacitance and the resistance of sample 17. It was also found that by insulating probe 12 using electric insulative material 20, $V_2$ was found to depend on the effective capacitance alone. This can be understood based on the above discussion, substituting $R_{eff}$ for a very large value, or infinity. This approach has a great advantage as it was found that voltage $V_2$ is almost independent of the sample temperature and salinity within experimental errors. On the other hand, the experiments also showed that the effective resistance depends on the temperature as well as the sample salinity, in agreement with known data. This dictates the measurements of temperature of the sample simultaneously with $V_1$ to get meaningful calibrations. Thus, if the user would like to measure the salinity of a given sample, they would use probe 12 without insulative material 20. If the user would like to measure moisture contents or sample capacitance only, they would use probe 12 with insulative material 20. For scientific measurements of moisture contents, referring to FIG. 3 one can get highly reliable data by using probes 12 with and without insulative material 20 simultaneously, each probe connected to a pulse generator 22 and a measuring device 30. The actual configuration will depend on the hardware available. As shown, it is convenient to connect probes 12 to the same pulse generator 22 in parallel, although different pulse generators 22 could be used if different pulses are desired. Also as shown, individual measuring devices are used for each probe 12. It will be understood that this can be combined into one measuring device 30. If a microprocessor 46 is used as measuring device 30, this may be done, for example, by staggering the sampling in time. If discrete components are used, it may be necessary to provide a separate circuit for each. It will be understood that, as an extension to this arrangement, more probes 12 may be included for example, either to obtain an average of a plot of land, or to characterize the properties in a plot of land.

Apparatus 10 as described above is intended primarily for measuring soil samples. It has the advantage that it can be made very small (less than 3 mm wide) for minimal ground disturbance. It has been designed to be used in remotes sites to study natural soils for a few months at a time. Hence, energy conservation is essential to run the device, using batteries, solar cells, or a combination as the energy source.

Operation:

The use and operation of apparatus for determining properties of a sample 10 will now be discussed with reference to FIGS. 1 through 10. Referring now to FIGS. 1 and 2, probe 12 either with or without electrically insulative material 20 is inserted into sample 17, with pulse generator 22 connected to input 14 and a measuring device 30 connected to output 16 of probe 12. Referring to FIG. 8, pulses 24 are generated with a square leading edge 28 and a period T of a sufficient duration to allow probe 12 to reach steady state. Referring to FIGS. 8 and 9, the output waveform 38 across resistor 36 can then be used to determine the effective resistance $R_{eff}$ and the effective capacitance $C_{eff}$ of probe 12 if it is not coated, or just $C_{eff}$ if it is coated with insulative material 20. As illustrated in FIG. 6, measuring device 30 is connected including capacitive elements 40 and 44, a resistive element 32, and a diode 42, connected as shown. Alternatively, measuring device 30 may comprise a microprocessor 46 to perform the same functions. It will be understood that a combination of discrete components and microprocessor 46 may also be used to act as a measuring device 30. For example, sampling by microprocessor 46 may occur across resistor 32.

Once the measurements are taken, measuring device 30 will output the properties being measured, having been calibrated previously based on known values and the corresponding readings. When determining the properties, it may be preferable not to display the effective capacitance and resistance, but rather calculate and display the desired physical properties directly. Methods for accomplishing these aspects will be known to those skilled in the art.

In this patent document, the word "comprising" is used in its non-limiting sense to mean that items following the word are included, but items not specifically mentioned are not excluded. A reference to an element by the indefinite article "a" does not exclude the possibility that more than one of the element is present, unless the context clearly requires that there be one and only one of the elements.

The embodiments of the invention in which an exclusive property or privilege is claimed are defined as follows:

1. An apparatus for determining properties of a sample, the apparatus comprising:
   a first probe having an input, an output and two conductors uncoated with any electrically insulative material, and the first probe having an effective capacitance and an effective resistance;
   a second probe having an input, an output and two conductors coated with an electrically insulative material, and the second probe having an effective capacitance and an effective resistance;
   a pulse generator, for producing square pulses, being connected to the input of the first probe and the input of the second probe, such that the square pulses are produced at the input of the first probe and the second probe, each square pulse having a constant voltage and a period of sufficient duration to allow a voltage across the effective resistance and the effective capacitance of the two conductors of the first probe and the effective resistance and the effective capacitance of the two coated conductors of the second probe to reach steady state;
   a measuring device being connected to the output of the first probe and the output of the second probe and configured to output a representation of the properties of a sample based on the effective resistance and the effective capacitance of the first probe and the second probe; and
   a capacitive element that acts as a simple integrator and a resistive element in series the capacitive element, such that the effective resistance $R_{eff}$ is estimated using formula $R_{eff}=[(V_{applied}/\Delta V)-1]R$, and such that the effective capacitance $C_{eff}$ is estimated using $$C_{eff} = -\frac{\ln[V_C(t)/V_{max}]}{t/R_{discharge}},$$

where $V_{applied}$ is the voltage of the square pulse, $\Delta V$ is the steady state voltage of the resistive element R is the resistance of the resistive element, $V_c(t)$ is the voltage response of the capacitive element, $V_{max}$ is the voltage of the square pulse less $\Delta V$, t is the time required to discharge the capacitor after the square pulse, and $R_{discharge}=[R \cdot R_{eff}/(R+R_{eff})]$.

2. The apparatus of claim 1, wherein the two conductors of the first probe are substantially parallel and separated by a known distance (d).

3. The apparatus of claim 2, wherein the two conductors of the second probe are substantially parallel and separated by the known distance (d).

4. The apparatus of claim 1, wherein the properties of the sample are selected from a group consisting of the moisture content, salinity, resistance, inductance and capacitance.

5. The apparatus of claim 1, wherein the measuring device comprises one of a diode or a semiconductor switch connected in series with a capacitive element that acts as an integrator during a discharge cycle, such that a value of the steady state of the voltage of the capacitive element depends on the effective capacitance and effective resistance of the first and the second probes.

6. The apparatus of claim 1, wherein the measuring device comprises a microprocessor.

7. The apparatus of claim 5, determines a moisture of a sample independent of the salinity.

8. The apparatus of claim 1, wherein the square pulse has a square leading edge.

9. A method for determining properties of a sample, the method comprising the steps of:
   inserting a first probe into the sample with the first probe having an input, an output and two conductors coated with an electrically insulative material, and the first probe having an effective capacitance and an effective resistance dependent upon the properties of the sample;
   generating a square pulse at the input of the first probe, the square pulse having a period of a sufficient duration to allow a voltage across the effective resistance and the effective capacitance of the first probe to reach steady state;
   connecting a measuring device to the output of the first probe, the measuring device configured to output a representation of the properties of the sample based on the effective resistance and the effective capacitance of the first probe; and
   utilizing a capacitive element as the measuring device to acts as an integrator and a resistive element parallel with the capacitive element such that the effective resistance $R_{eff}$ is estimated using formula $R_{eff}=[(V_{applied}/\Delta V)-1]R$, and such that the effective capacitance $C_{eff}$ is estimated using $$C_{eff} = -\frac{\ln[V_C(t)/V_{max}]}{t/R_{discharge}},$$

where $V_{applied}$ is the voltage of the square pulse, $\Delta V$ is the steady state voltage of the resistive element, R is the resistance of the resistive element, $V_C(t)$ is thevoltage response of the capacitive element $V_{max}$ is the voltage of the square pulse less $\Delta V$, t is the time required to discharge the capacitor after the square pulse, and $R_{discharge}=[R \cdot R_{eff}/(R+R_{eff})]$.

10. The method of claim 9, further comprising the step of measuring a moisture content, a salinity, a resistance, and a capacitance of the sample.

11. The method of claim 9, further comprising the step of forming the measuring device with a diode connected in series with a capacitive element, such that the capacitive element acts as an integrator during a discharge cycle, such that a steady state value of the voltage of the capacitive element depends on the effective capacitance and effective resistance of the first probe.

12. The method of claim 9, further comprising the step of utilizing a microprocessor as the measuring device.

13. The method of claim 9, further comprising the step of forming the first probe to have two parallel conductors spaced apart at a known distance (d).

14. The method of claim 9, further comprising the step of determining a moisture level of a sample independent of a salinity level.

15. The method of claim 9, further comprising the step of arranging the two conductors coated with an electrically insulative material to be parallel and spaced apart at a known distance (d).

16. The method of claim 9, further comprising the step of inserting a second probe into the sample, and the second probe having an input, an output, two parallel conductors uncoated with electrically insulative material, and an effective capacitance and an effective resistance.

17. The method of claim 9, further comprising the step of generating the square pulse having a square leading edge.

* * * * *